United States Patent
Clayman et al.

(10) Patent No.: US 6,849,069 B1
(45) Date of Patent: *Feb. 1, 2005

(54) MEDICAL DEVICE WITH TAIL(S) FOR ASSISTING FLOW OF URINE

(75) Inventors: Ralph V. Clayman, Clayton, MO (US); Alyssa J. Dassa, Wayne, NJ (US); Christopher Fishbein, Norfolk, MA (US); Douglas E. Godshall, Franklin, MA (US); Willet F. Whitmore, III, Sarasota, FL (US)

(73) Assignee: Boston Scientitfic Corporation, Natick, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/743,885

(22) Filed: Nov. 6, 1996

Related U.S. Application Data
(60) Provisional application No. 60/006,259, filed on Nov. 7, 1995, provisional application No. 60/009,983, filed on Jan. 16, 1996, and provisional application No. 60/025,284, filed on Sep. 19, 1996.

(51) Int. Cl.⁷ .......................... A61M 27/00; A61M 1/00; A61F 2/36
(52) U.S. Cl. .................... 604/544; 604/317; 623/23.64; 623/23.7
(58) Field of Search ............................. 604/8–10, 517, 604/317, 327, 328, 540, 541, 543, 544, 93.01, 264, 523; 623/23.7, 23.64, 23.65, 23.66

(56) References Cited

U.S. PATENT DOCUMENTS
191,775 A    6/1877  Parsons (List continued on next page.)

FOREIGN PATENT DOCUMENTS
CA    1092927    1/1981

(List continued on next page.)

OTHER PUBLICATIONS
Mardis et al., "Comparative Evaluation of Materials Used for Internal Ureteral Stents," *Journal of Endourology*, 1993, vol. 7, No. 2, (pp. 105–113).

(List continued on next page.)

*Primary Examiner*—Brian L. Casler
*Assistant Examiner*—Catherine Serke
(74) *Attorney, Agent, or Firm*—Testa, Hurwitz & Thibeault, LLP

(57) ABSTRACT

A ureteral stent for assisting movement of urine along a patient's ureter and into the patient's bladder. The stent includes an elongated tubular segment extending toward the bladder from a kidney end region for placement in the renal cavity to a bladder end region. A central lumen connects at least one opening at the first end region to at least one opening in the bladder end region. Thin flexible tail(s) are attached to the bladder end region of the tubular segment at a point outside the bladder so as to receive urine from the opening in the bladder end region of the tubular segment and to transport urine from there across the ureter/bladder junction and into the bladder. The tails include an elongated external urine-transport surface sized and configured to transport urine along the ureter. The urine transporting surface(s) are sized and configured to extend along at least part of the ureter, across the ureter/bladder junction, and from there into the bladder.

11 Claims, 10 Drawing Sheets

U.S. PATENT DOCUMENTS

| | | | |
|---|---|---|---|
| 256,590 A | 4/1882 | Pfarre | |
| 386,603 A | 7/1888 | Parsons | |
| 559,620 A | 5/1896 | Shearer | |
| 1,211,928 A | 1/1917 | Fisher | |
| 2,257,369 A | 9/1941 | Davis | 128/349 |
| 3,087,493 A | 4/1963 | Schossow | 128/351 |
| 3,314,430 A | 4/1967 | Alley et al. | 128/350 |
| 3,359,974 A | 12/1967 | Khalil | 128/2.05 |
| 3,394,705 A | 7/1968 | Abramson | 128/349 |
| 3,437,088 A | 4/1969 | Bielinski | 128/2 |
| 3,485,234 A | 12/1969 | Stevens | 128/2 |
| 3,593,713 A | 7/1971 | Bogoff et al. | 128/246 |
| 3,612,050 A | 10/1971 | Sheridan | 128/214.4 |
| 3,633,579 A | 1/1972 | Alley et al. | 128/214.4 |
| 3,726,281 A | 4/1973 | Norton et al. | 128/349 R |
| 3,746,003 A | 7/1973 | Blake et al. | 128/349 B |
| 3,788,326 A | 1/1974 | Jacobs | 128/305 |
| 3,828,767 A | 8/1974 | Spiroff | 128/2.05 |
| 3,902,492 A | 9/1975 | Greenhalgh | 128/241 |
| 3,906,954 A | 9/1975 | Baehr et al. | 128/305 |
| 3,920,023 A | 11/1975 | Dye et al. | 128/347 |
| 3,995,623 A | 12/1976 | Blake et al. | 128/2.06 E |
| 4,004,588 A | 1/1977 | Alexander | 128/241 |
| 4,037,599 A | 7/1977 | Raulerson | 128/214.4 |
| 4,065,264 A | 12/1977 | Lewin | 23/258.5 BH |
| 4,069,814 A | 1/1978 | Clemens | 128/2 F |
| 4,096,860 A | 6/1978 | McLaughlin | 128/214.4 |
| 4,099,528 A | 7/1978 | Sorenson et al. | 128/214.4 |
| 4,100,246 A | 7/1978 | Frisch | 264/230 |
| 4,129,129 A | 12/1978 | Amrine | 128/214 |
| 4,134,402 A | 1/1979 | Marhurkar | 128/214 |
| 4,138,288 A | 2/1979 | Lewin | 195/1.8 |
| 4,138,457 A | 2/1979 | Rudd et al. | 264/500 |
| 4,144,884 A | 3/1979 | Tersteegen et al. | 128/214.4 |
| 4,149,535 A | 4/1979 | Volder | 128/214.4 |
| 4,168,703 A | 9/1979 | Kenigsberg | 128/748 |
| 4,173,981 A | 11/1979 | Mortensen | 128/348 |
| 4,180,068 A | 12/1979 | Jacobsen et al. | 128/214 R |
| 4,182,739 A | 1/1980 | Curtis | 422/47 |
| 4,183,961 A | 1/1980 | Curtis | 424/366 |
| 4,202,332 A | 5/1980 | Tersteegen et al. | 128/214.4 |
| 4,203,436 A | 5/1980 | Grimsrud | 128/214 R |
| 4,212,304 A | 7/1980 | Finney | 128/349 |
| 4,217,895 A | 8/1980 | Sagae et al. | 128/214.4 |
| 4,223,676 A | 9/1980 | Wuchinich et al. | 128/276 |
| 4,236,520 A | 12/1980 | Anderson | 128/348 |
| 4,239,042 A | 12/1980 | Asai | 128/214.4 |
| 4,257,416 A | 3/1981 | Prager | 128/214 R |
| 4,270,535 A | 6/1981 | Bogue et al. | 128/214.4 |
| 4,307,723 A * | 12/1981 | Finney | 604/8 |
| 4,327,722 A | 5/1982 | Groshong et al. | 128/214.4 |
| 4,334,327 A | 6/1982 | Lyman et al. | 3/1 |
| 4,385,631 A | 5/1983 | Uthmann | 604/284 |
| 4,403,983 A | 9/1983 | Edelman et al. | 604/43 |
| 4,405,313 A | 9/1983 | Sisley et al. | 604/43 |
| 4,405,314 A | 9/1983 | Cope | 604/51 |
| 4,406,656 A | 9/1983 | Hattler et al. | 604/280 |
| 4,413,989 A | 11/1983 | Schjeldahl et al. | 604/96 |
| 4,419,094 A | 12/1983 | Patel | 604/93 |
| D272,651 S | 2/1984 | Marhurkar | D24/54 |
| 4,443,333 A | 4/1984 | Marhurkar | 210/87 |
| 4,451,252 A | 5/1984 | Martin | 604/43 |
| 4,456,000 A | 6/1984 | Schjeldahl et al. | 128/1 D |
| 4,484,585 A | 11/1984 | Baier | 128/748 |
| 4,493,696 A | 1/1985 | Uldall | 604/43 |
| 4,504,264 A | 3/1985 | Kelman | 604/22 |
| RE31,873 E | 4/1985 | Howes | 128/674 |
| 4,531,933 A | 7/1985 | Norton et al. | |
| 4,540,402 A | 9/1985 | Aigner | 604/44 |
| 4,543,087 A | 9/1985 | Sommercorn et al. | 604/43 |
| 4,559,046 A | 12/1985 | Groshong et al. | 604/282 |
| 4,563,170 A | 1/1986 | Aigner | 604/5 |
| 4,568,329 A | 2/1986 | Marhurkar | 604/43 |
| 4,568,338 A | 2/1986 | Todd | 604/281 |
| 4,581,012 A | 4/1986 | Brown et al. | 604/43 |
| 4,583,968 A | 4/1986 | Marhurkar | 604/43 |
| 4,596,548 A | 6/1986 | DeVries et al. | 604/4 |
| 4,601,697 A | 7/1986 | Mammolenti et al. | 604/43 |
| 4,601,701 A | 7/1986 | Mueller, Jr. | 604/83 |
| 4,608,993 A | 9/1986 | Albert | 128/663 |
| 4,610,657 A * | 9/1986 | Densow | 604/8 |
| 4,619,643 A | 10/1986 | Bai | 604/43 |
| 4,623,327 A | 11/1986 | Marhurkar | 604/4 |
| 4,626,240 A | 12/1986 | Edelman et al. | 604/43 |
| 4,643,711 A | 2/1987 | Bates | 604/4 |
| 4,643,716 A | 2/1987 | Drach | 604/8 |
| 4,648,865 A | 3/1987 | Aigner | 604/5 |
| 4,666,426 A | 5/1987 | Aigner | 604/5 |
| 4,671,795 A | 6/1987 | Mulchin | |
| 4,675,004 A | 6/1987 | Hadford et al. | 604/44 |
| 4,682,978 A | 7/1987 | Martin | 604/43 |
| 4,687,471 A | 8/1987 | Twardowski et al. | 604/175 |
| 4,692,141 A | 9/1987 | Marhurkar | 604/43 |
| 4,694,838 A | 9/1987 | Wijayarthna et al. | 128/658 |
| 4,713,049 A | 12/1987 | Carter | 604/8 |
| 4,722,725 A | 2/1988 | Sawyer et al. | 604/27 |
| 4,737,146 A | 4/1988 | Amaki et al. | 604/51 |
| 4,738,667 A | 4/1988 | Galloway | 604/281 |
| 4,747,840 A | 5/1988 | Ladika et al. | 604/281 |
| 4,753,640 A | 6/1988 | Nichols et al. | 604/247 |
| 4,755,176 A | 7/1988 | Patel | 604/280 |
| 4,769,005 A | 9/1988 | Ginsburg et al. | 604/53 |
| 4,770,652 A | 9/1988 | Mahurkar | 604/4 |
| 4,772,268 A | 9/1988 | Bates | 604/174 |
| 4,773,432 A | 9/1988 | Rydell | 128/772 |
| 4,776,841 A | 10/1988 | Catalano | 604/43 |
| 4,787,884 A | 11/1988 | Goldberg | 604/8 |
| 4,790,809 A * | 12/1988 | Kuntz | 604/8 |
| 4,790,810 A | 12/1988 | Pugh, Jr. et al. | 604/8 |
| 4,795,439 A | 1/1989 | Guest | 604/43 |
| 4,808,155 A | 2/1989 | Marhurkar | 604/43 |
| 4,809,710 A | 3/1989 | Williamson | 128/748 |
| 4,813,429 A | 3/1989 | Eshel et al. | 128/736 |
| 4,813,925 A | 3/1989 | Anderson, Jr. et al. | 604/8 |
| 4,820,262 A | 4/1989 | Finney | 604/8 |
| 4,822,345 A | 4/1989 | Danforth | 604/282 |
| 4,838,881 A | 6/1989 | Bennett | 604/280 |
| 4,842,582 A | 6/1989 | Marhurkar | 604/43 |
| 4,842,590 A | 6/1989 | Tanabe et al. | 604/282 |
| 4,846,791 A | 7/1989 | Hattler et al. | 604/43 |
| 4,846,814 A | 7/1989 | Ruiz | 604/281 |
| 4,863,442 A | 9/1989 | DeMello et al. | 604/282 |
| 4,874,360 A * | 10/1989 | Goldberg et al. | 604/8 |
| 4,887,996 A | 12/1989 | Bengmark | 604/54 |
| 4,894,057 A | 1/1990 | Howes | 604/280 |
| 4,895,561 A | 1/1990 | Mahurkar | 604/43 |
| 4,913,683 A | 4/1990 | Gregory | |
| 4,931,037 A | 6/1990 | Wetterman | 604/8 |
| 4,950,228 A | 8/1990 | Knapp, Jr. et al. | 604/8 |
| 4,960,409 A | 10/1990 | Catalano | 604/53 |
| 4,960,411 A | 10/1990 | Buchbinder | 604/95 |
| 4,961,809 A | 10/1990 | Martin | 156/294 |
| 4,963,129 A * | 10/1990 | Rusch | 604/8 |
| 4,981,482 A | 1/1991 | Ichikawa | 606/108 |
| 4,985,022 A | 1/1991 | Fearnot et al. | 604/682 |
| 4,986,814 A | 1/1991 | Burney et al. | 604/164 |
| 4,990,133 A | 2/1991 | Solazzo | 604/8 |
| 4,995,863 A | 2/1991 | Nichols et al. | 604/247 |
| 4,995,865 A | 2/1991 | Gahara et al. | 604/43 |
| 4,995,868 A | 2/1991 | Brazier | 604/105 |
| 4,998,919 A | 3/1991 | Schnepp-Pesch et al. | 604/164 |

| | | | | | | |
|---|---|---|---|---|---|---|
| 5,009,636 A | 4/1991 | Wortley et al. ............... 604/43 | | 5,405,341 A | 4/1995 | Martin ..................... 604/284 |
| 5,013,296 A | 5/1991 | Buckberg et al. ............. 604/44 | | 5,411,490 A | 5/1995 | Tennican et al. ............ 604/236 |
| 5,019,102 A | 5/1991 | Hoene ......................... 623/12 | | 5,440,327 A | 8/1995 | Stevens ...................... 346/46 |
| 5,029,580 A | 7/1991 | Radford et al. ........ 128/207.14 | | 5,451,206 A | 9/1995 | Young ......................... 604/43 |
| 5,041,083 A | 8/1991 | Tsuchida et al. .............. 604/43 | | 5,464,398 A | 11/1995 | Haindl ..................... 604/280 |
| 5,053,004 A | 10/1991 | Markel et al. ................. 604/43 | | 5,470,322 A | 11/1995 | Horzewski et al. ......... 604/280 |
| 5,053,023 A | 10/1991 | Martin ...................... 604/280 | | 5,472,417 A | 12/1995 | Martin et al. ................. 604/43 |
| 5,057,073 A | 10/1991 | Martin ........................ 604/43 | | 5,472,432 A | 12/1995 | Martin ..................... 604/248 |
| 5,116,309 A | 5/1992 | Coll .............................. 604/8 | | 5,480,380 A | 1/1996 | Martin ....................... 604/43 |
| 5,124,127 A | 6/1992 | Jones et al. ................... 422/46 | | 5,486,159 A | 1/1996 | Maharkur ..................... 604/4 |
| 5,129,910 A | 7/1992 | Phan et al. ................. 606/127 | | 5,489,278 A | 2/1996 | Abrahamson ............... 604/280 |
| 5,135,487 A | 8/1992 | Morrill et al. ................ 604/96 | | 5,509,897 A | 4/1996 | Twardowski et al. ......... 604/43 |
| 5,135,599 A | 8/1992 | Martin et al. ............... 156/294 | | 5,514,100 A | 5/1996 | Marhurkar ................ 604/195 |
| 5,141,499 A * | 8/1992 | Zappacosta ................. 604/175 | | 5,514,176 A | 5/1996 | Bosley, Jr. ..................... 623/1 |
| 5,141,502 A | 8/1992 | Macaluso, Jr. .............. 604/281 | | 5,522,807 A | 6/1996 | Luther ...................... 604/264 |
| 5,149,330 A | 9/1992 | Brightbill ................... 604/280 | | 5,527,337 A | 6/1996 | Stack et al. ................. 606/198 |
| 5,156,592 A | 10/1992 | Martin et al. ................ 604/43 | | 5,531,741 A | 7/1996 | Barbacci ...................... 606/15 |
| 5,156,596 A | 10/1992 | Balbierz et al. ............. 604/164 | | 5,554,136 A | 9/1996 | Luther ...................... 604/264 |
| 5,160,325 A | 11/1992 | Nichols et al. .............. 604/247 | | 5,556,390 A | 9/1996 | Hicks ....................... 604/280 |
| 5,167,623 A | 12/1992 | Cianci et al. ................. 604/43 | | 5,569,182 A | 10/1996 | Twardowski et al. ......... 604/43 |
| 5,171,216 A | 12/1992 | Dasse et al. .................. 604/43 | | 5,569,184 A | 10/1996 | Crocker et al. ............... 604/53 |
| 5,176,625 A | 1/1993 | Brisson .......................... 604/8 | | 5,569,195 A | 10/1996 | Saab .......................... 604/96 |
| 5,176,626 A * | 1/1993 | Soehendra | | 5,571,093 A | 11/1996 | Cruz et al. .................. 604/270 |
| 5,178,803 A | 1/1993 | Tsuchida et al. .............. 264/23 | | 5,573,508 A | 11/1996 | Thornton ..................... 604/96 |
| 5,188,593 A | 2/1993 | Martin ........................ 604/43 | | 5,599,291 A | 2/1997 | Balbierz et al. ................. 604/8 |
| 5,190,520 A | 3/1993 | Fenton, Jr. et al. ........... 604/43 | | 5,613,980 A | 3/1997 | Chauhan ................... 606/194 |
| 5,195,962 A | 3/1993 | Martin et al. ................. 604/43 | | 5,624,413 A | 4/1997 | Markel et al. ............. 604/280 |
| 5,197,951 A | 3/1993 | Marhurkar ................... 604/93 | | 5,630,794 A | 5/1997 | Lax et al. ..................... 604/22 |
| 5,207,648 A | 5/1993 | Gross ......................... 604/164 | | 5,643,222 A | 7/1997 | Marhurkar ................. 604/195 |
| 5,209,723 A | 5/1993 | Twardowski et al. ......... 604/43 | | 5,647,843 A * | 7/1997 | Mesrobian et al. |
| 5,211,627 A | 5/1993 | William ....................... 604/82 | | 5,649,909 A | 7/1997 | Cornelius .................... 604/96 |
| 5,221,253 A | 6/1993 | Coll .............................. 604/8 | | 5,653,689 A | 8/1997 | Buelna et al. ................ 604/96 |
| 5,221,255 A | 6/1993 | Marhurkar et al. ........... 604/43 | | 5,681,274 A | 10/1997 | Perkins et al. ................. 604/8 |
| 5,221,256 A | 6/1993 | Mahurkar .................... 604/43 | | 5,683,640 A | 11/1997 | Miller et al. ................ 264/255 |
| 5,234,663 A | 8/1993 | Jones et al. ................... 422/46 | | 5,685,862 A | 11/1997 | Marhurkar ................. 604/194 |
| 5,240,677 A | 8/1993 | Jones et al. ................... 422/46 | | 5,685,867 A | 11/1997 | Twardowski et al. ....... 604/280 |
| 5,242,395 A | 9/1993 | Maglinte ..................... 604/96 | | 5,695,479 A | 12/1997 | Jagpal ........................ 604/264 |
| 5,250,038 A | 10/1993 | Melker et al. .............. 604/264 | | 5,769,868 A | 6/1998 | Yock ......................... 604/194 |
| 5,261,879 A | 11/1993 | Brill ............................ 604/96 | | 5,792,105 A | 8/1998 | Lin et al. ...................... 604/96 |
| 5,269,802 A * | 12/1993 | Garber .......................... 604/8 | | 5,795,326 A | 8/1998 | Siman ......................... 604/43 |
| 5,275,597 A | 1/1994 | Higgins et al. ............... 606/33 | | 5,830,184 A | 11/1998 | Basta ........................ 604/104 |
| 5,279,560 A | 1/1994 | Morrill et al. ................ 604/96 | | 5,830,196 A | 11/1998 | Hicks ........................ 604/280 |
| 5,282,784 A | 2/1994 | Willard .......................... 604/8 | | 5,843,028 A | 12/1998 | Weaver et al. ................ 604/54 |
| 5,292,305 A | 3/1994 | Boudewijn et al. ........... 604/43 | | | | |
| 5,295,954 A | 3/1994 | Sachse .......................... 604/8 | | | | |
| 5,308,322 A | 5/1994 | Tennican et al. .............. 604/83 | | | | |
| 5,318,532 A | 6/1994 | Frassica ....................... 604/96 | | | | |
| 5,324,274 A | 6/1994 | Martin ...................... 604/248 | | | | |
| 5,330,449 A | 7/1994 | Prichard et al. ............. 604/282 | | | | |
| 5,338,311 A | 8/1994 | Marhurkar ................. 604/195 | | | | |
| 5,342,301 A | 8/1994 | Saab ........................... 604/96 | | | | |
| 5,346,467 A * | 9/1994 | Coll .............................. 604/8 | | | | |
| 5,346,471 A | 9/1994 | Raulerson .................... 604/43 | | | | |
| 5,348,536 A | 9/1994 | Young et al. ................. 604/43 | | | | |
| 5,354,263 A * | 10/1994 | Coll .............................. 604/8 | | | | |
| 5,358,689 A | 10/1994 | Jones et al. ................... 422/46 | | | | |
| 5,360,397 A | 11/1994 | Pinchuk ....................... 604/27 | | | | |
| 5,364,340 A | 11/1994 | Coll .............................. 604/8 | | | | |
| 5,364,344 A | 11/1994 | Beattie et al. ................. 604/43 | | | | |
| 5,366,464 A | 11/1994 | Belknap ..................... 606/159 | | | | |
| 5,372,600 A | 12/1994 | Beyar et al. ................. 606/108 | | | | |
| 5,374,245 A | 12/1994 | Marhurkar ................... 604/43 | | | | |
| 5,378,230 A | 1/1995 | Marhurkar ................... 604/43 | | | | |
| 5,380,270 A | 1/1995 | Ahmadzadeh ..................... 1/1 | | | | |
| 5,380,276 A | 1/1995 | Miller et al. .................. 604/28 | | | | |
| 5,395,316 A | 3/1995 | Martin ......................... 604/43 | | | | |
| 5,399,172 A | 3/1995 | Martin et al. ............... 604/248 | | | | |
| 5,401,257 A | 3/1995 | Chevalier, Jr. et al. ...... 604/265 | | | | |
| 5,403,291 A | 4/1995 | Abrahamson ............... 604/280 | | | | |
| 5,405,320 A | 4/1995 | Twardowski et al. ......... 604/43 | | | | |
| 5,405,329 A | 4/1995 | Durand ....................... 604/164 | | | | |

FOREIGN PATENT DOCUMENTS

| | | | |
|---|---|---|---|
| CA | 1150122 | 7/1983 | |
| CA | 1167727 | 5/1984 | |
| CA | 1193508 | 9/1985 | |
| CA | 1219785 | 3/1987 | |
| CA | 1225299 | 11/1987 | |
| DE | 2259865 | 6/1974 | |
| DE | 3112762 C2 | 1/1983 | |
| DE | 35 17 813 A1 | 11/1986 | |
| DE | 3517813 A1 * | 11/1986 | .......... A61M/27/00 |
| DE | 3740288 C1 * | 4/1989 | |
| DE | 37 40 288 C1 | 4/1989 | |
| DE | 3740288 C1 * | 4/1989 | .......... A61M/27/00 |
| DE | 41 03 573 A1 | 8/1992 | |
| DE | 41 34 030 A1 | 4/1993 | |
| DE | 9314585 | 1/1994 | |
| EP | 0036642 A2 | 9/1981 | |
| EP | 0079719 A1 | 5/1983 | |
| EP | 0101890 B1 | 3/1984 | |
| EP | 0144525 A2 | 6/1985 | |
| EP | 0168136 A1 | 1/1986 | |
| EP | 0183421 A2 | 6/1986 | |
| EP | 0101890 A1 | 9/1986 | |
| EP | 326 908 A2 | 8/1989 | |
| EP | 0333308 A2 | 9/1989 | |
| EP | 0183421 B1 | 4/1990 | |
| EP | 0386408 A1 | 9/1990 | |

| | | |
|---|---|---|
| EP | 0490459 A1 | 6/1992 |
| EP | 0490459 B1 | 6/1992 |
| EP | 0554722 A | 8/1993 |
| EP | 0876803 | 11/1998 |
| FR | 1285953 | 1/1962 |
| FR | 1508959 | 12/1967 |
| FR | 2297640 A1 | 8/1976 |
| FR | 2530958 A1 | 2/1984 |
| FR | 2611486 | 9/1988 |
| GB | 2017499 A | 10/1979 |
| GB | 2156220 A | 10/1985 |
| GB | 2235384 A | 3/1991 |
| JP | 57-90150 | 6/1982 |
| JP | 57-90150 * | 6/1982 |
| WO | WO 84/04043 | 10/1984 |
| WO | WO 95/26763 | 10/1995 |
| WO | WO 95/35130 | 12/1995 |
| WO | WO 97/10858 | 3/1997 |
| WO | WO 97/17094 | 5/1997 |
| WO | 9717094 | 5/1997 |
| WO | WO 97/37699 | 10/1997 |
| WO | WO 97/37718 | 10/1997 |

OTHER PUBLICATIONS

"Uresteroscopic Procedures—Technical Advances," *Color Atlas/Text of Ureteroscopy*, 1993 New York, Igaku–Shoin, p. 281.

Collier et al., "Proximal Stent Displacement As Complication of Pigtail Ureteral Stent," *Urology*, Apr. 1979, vol. XIII, No. 4, (pp. 372–375).

Birch et al., "Tethered Ureteric Stents—a Clinical Assessment," *British Journal of Urology*, 1988, 62, (pp. 409–411).

Mardis et al., "Guidewires, Ureteral Catheters, and Stents," *Color Atlas/Text of Ureteroscopy*, New York, Igaku–Shoin, Ch. 5, (pp. 65–84).

Cook Urological product brochure, "Ureteral Stents," 1987, (pp. 3–23; last page).

Cook Urological catalog, "Urological Surgical Product," 1990–1991, (pp. 1–3, 7–29, 48–148; last page).

Bard/angiomed product brochure, 1988.

Cook Urological Catalog, 1995, (pp. 1–2, 9–41, 63–173; last page).

Mardis et al., "Ureteral Stents–Materials," *Urologic Clinics of North America* Aug. 1988, vol. 15, No. 3, (pp. 471–479).

Mardis et al., "Ureteral Stents Use and Complications," *Problems in Urology*, Jun. 1992 vol. 6, No. 2, (pp. 296–306).

Hackethorn et al., "Antegrade Internal Ureteral Stenting: A Technical Refinement," *Radiology*, Jul. 1985, vol. 156, No. 3, (pp. 287–288).

Rutner et al., "Percutaneous Pigtail Nephrostomy," *Urology*, Oct. 1979, vol. XIV, No. 4, (pp. 337–340).

Mardis, "Evaluation of Polymeric Materials for Endourologic Devices," *Seminars in Interventional Radiology*, Mar. 1987, vol. 4, No. 1, (pp. 36–45).

Mardis et al., "Double Pigtail Ureteral Stent," *Urology*, Jul. 1979, vol. XIV, No. 1, (pp. 23–26).

Hepperlen et al., "Self–Retained Internal Ureteral Stents: A New Approach," *The Journal of Urology*, Jun. 1978, vol. 119, (pp. 731–734).

Culkin, "Complications of Ureteral Stents," *Infections in Urology*, Sep./Oct. 1996, (pp. 139–143).

Sadlowski et al., "New Technique For Percutaneous Nephrostomy Under Ultrasound Guidance," *Journal of Urology*, May 1979, vol. 121, (pp. 559–561).

Camacho et al. "Double–Ended Pigtail Ureteral Stent: Useful Modifcation to Single End Ureteral Stent," *Urology*, May 1979, vol. XIII, No. 5, (pp. 516–520).

Bigongiari et al., "Conversion of Percutaneous Ureteral Stent To Indwelling Pigtail Stent Over Guidewire," *Urology*, May 1980, vol. XV, No. 5, (pp. 461–465).

Minkov et al., "Our Experience in the Application of the Biocompatible Indwelling Ureteral Stents" *International Urology and Nephrology*, 1986, 18 (4), (pp. 403–409).

Mardis et al., "Polyethylene Double–Pigtail Ureteral Stents," *Urologic Clinics of North America*, Feb. 1982, vol. 9, No. 1, (pp. 95–101).

Stables, "Percutaneous Nephrostomy: Techniques, Indications, and Results," *Urologic Clinics of North America*, Feb. 1982, vol. 9, No. 1, (pp. 15–29).

Bard Urological Division product catalog, 1990, (pp. 1–3, A1–A30, D7–D26; last page).

Cook Urological product brochure, "Filiform Ureteral Multi–Length Silicone Stent Sets," 1989.

Surgitek Brochure, "The Solution Is Perfectly Clear," 1990.

Bard brochure, "Introducing The Bard Urinary Diversion Stent," 1984.

Bard product brochure, "Stents To Satisfy The Urologist . . . ", 1988.

Bard product brochure, "Introducing The Bard Pediatric Urethral Stent,"1983.

Bard Access Systems Vas–Cath Incorporated Catalog (date unknown).

Cook Critical Care Catalog, "Products for Dialysis" pp. 3–15 (1989).

Cook Critical Care Catalog, "Uldall Double Lumen Hemodialysis Catheter Trays", date unknown.

Horizon Medical Products Catalog, date unkown.

McIntosh, et al. J.A.M.A. 169(8): 137–8 (1959).

Medcomp Catalog, "Hemodialysis Products" pp. 1–11, 14–16, 19–27, 30–36, date unknown.

Medcomp Catalog "Schon Twin–Cath", date unknown.

Quinton Instrument Co. Catalog, "Heterodialysis and Apheresis" (1994).

Quinton Instrument Co. Catalog, "Hemodialysis and Apheresis" (1995).

Quinton Instrument Co. Catalog, "Oncology/Critical Care" (1993).

Riesenfeld, et al. "Surface Modification of Functionally Active Heparin" Medical Technology (Mar. 1995).

"Triple Lumen Catheter" p. 3 (First! An Information Service of Individual, Inc., Sep. 25, 1995).

* cited by examiner

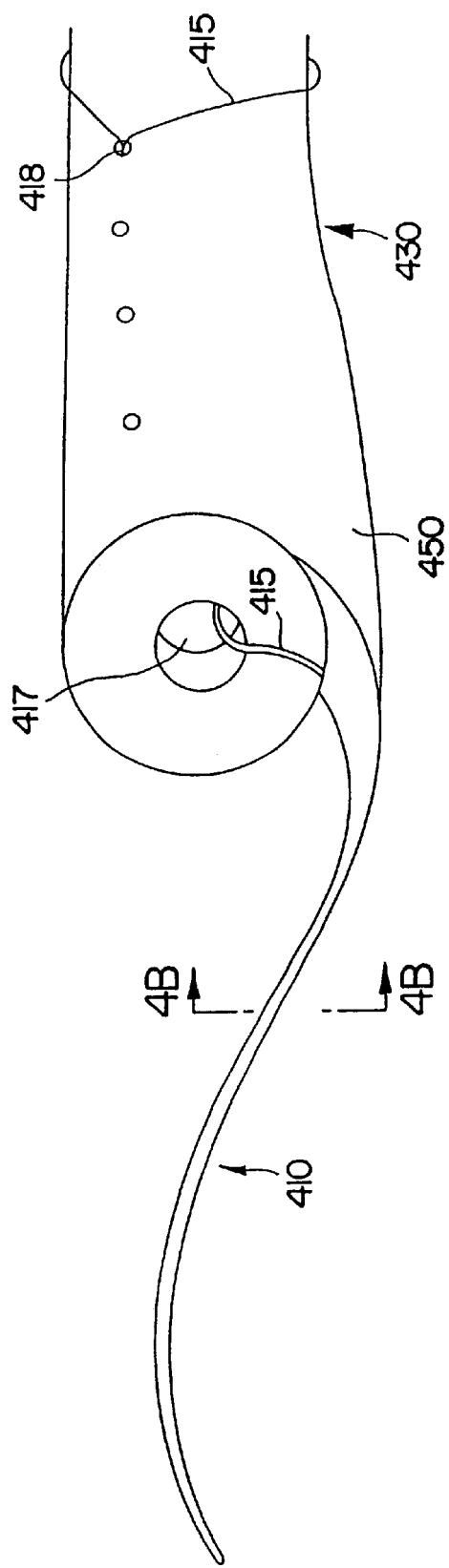
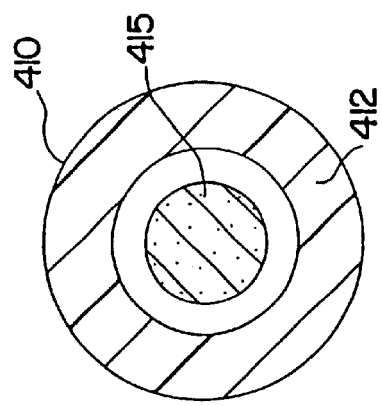
FIG. 4A
FIG. 4B

DETAIL OF THREADS

88 → ⊕

CONSEQUENCE OF THREADS
WHICH ARE TOO SOFT
(RUBBERY) IN COMPRESSION

MEDICAL DEVICE WITH TAIL(S) FOR ASSISTING FLOW OF URINE

CROSS-REFERENCE TO RELATED APPLICATIONS

This application is entitled under 35 U.S.C. § 119(e)(1) to the filing dates of earlier co-pending provisional applications U.S. Ser. No. 60/006,259, filed Nov. 7, 1995, U.S. Ser. No. 60/009,983 filed Jan. 16, 1996, and U.S. Ser. No. 60/025,284, filed Sep. 19, 1996.

FIELD OF THE INVENTION

This application relates to ureteral stents.

BACKGROUND OF THE INVENTION

Ureteral stents are used to assist urinary drainage from the kidney to the bladder in patients with ureteral obstruction or injury, or to protect the integrity of the ureter in a variety of surgical manipulations. More specifically, stents may be used to treat or avoid ureter obstructions (such as ureteral stones or ureteral tumors) which disrupt the flow of urine from the kidneys to the bladder. Serious obstructions may cause urine to back up into the kidneys, threatening renal function. Ureteral stents may also be used after endoscopic inspection of the ureter.

Ureteral stents typically are tubular in shape, terminating in two opposing ends: a kidney (upper) end and a bladder (lower) end. The ends may be coiled in a pigtail or J-shape to prevent the upward or downward migration of the stent, e.g., with physiological movements. The kidney coil is designed to retain the stent within the renal pelvis of the kidney and to prevent stent migration down the ureter. The bladder coil sits in the bladder and is designed to prevent stent migration upwards toward the kidney. The bladder coil is also used to aid in retrieval and removal of the stent.

Ureteral stents, particularly the portion positioned in the ureter near the bladder and inside the bladder, may produce adverse effects including blood in the urine, a continual urge to urinate, strangury, and flank pain accompanying reflux of urine up the stent (e.g., when voiding) as pressure within the bladder is transmitted to the kidney. In short, stents may cause or contribute to significant patient discomfort and serious medical problems.

FIG. 10 is a schematic drawing of the human urinary tract without a stent, showing the renal pelvis, the kidney, the ureter, and the ureteral orifices opening into the bladder. FIG. 11 depicts a typical double-J stent 10 which comprises a small tube 12 which sits inside the urinary system and assists the flow of urine from the kidney (renal pelvis) to the bladder. FIG. 12 depicts prior art indwelling ureteral stent 10 in position. Such stents are typically made of biocompatible plastic, coated plastic, or silicone material. Tube 12 typically varies in size from 4–8 fr. (mm in circumference), and it has multiple small holes throughout its length. A coiled shape pre-formed at each end 14 and 16 is designed to confine its movement within the urinary system, so that it will be maintained in the desired position. The upper (kidney) end 14 of the stent may be closed or tapered, depending on the method of insertion (e.g., the use of a guidewire). The tubular stent extends through the ureteral orifice 18a and into the bladder, fixing orifice 18a open, and thereby enhancing the opportunity for reflux. For clarity, the ureter entering bladder 20 through orifice 18b is not shown. A monofilament thread 22 may be attached to the bladder end of the stent for removal, usually without cystoendoscopy.

U.S. Pat. No. 4,531,933 ("the '933 patent") discloses a ureteral stent having helical coils at each end which are provided for preventing migration and expulsion.

SUMMARY OF THE INVENTION

We have discovered a ureteral stent design that avoids patient discomfort and urine reflux upward toward the kidney. Rather than rely on a tubular structure to contain and facilitate all (or, in some embodiments, any) urine flow along the ureter, the invention features a thin flexible elongated tail member having an elongated external urine-transport surface. Urine flows along the outside surface of the structure, between that surface and the inside wall of the ureter. Without limiting ourselves to a specific mechanism, it appears that urine may remain attached to, and flow along, the external urine transport surface. The use of a foreign body that is as small as possible in the lower (bladder) end of the ureter and in the bladder itself decreases patient discomfort. Typically, the external urine transport surface is sized and configured to extend along at least part of the ureter near the bladder, across the ureter/bladder junction, and from there through the ureteral opening into the bladder.

While most or all of the length of the stent may rely on such an external surface to assist flow, more typically the stent will also include an upper elongated tubular segment to transport urine along a significant portion of the upper ureter. The upper tubular segment is connected at its lower end to an elongated tail which has the above described external urine-transport surface. The upper tubular segment comprises: a) an upper region having at least a first opening; b) a lower region having at least a second opening to be positioned in the ureter outside the bladder, and c) a central lumen connecting the first opening to the second opening. The elongated tail is a thin flexible tail member or filament(s) extending from the lower region of the tubular segment at a point outside the bladder so as to receive urine from the second opening of the tubular segment and to transport urine along the ureter from the lower region of the tubular segment across the ureter/bladder junction and into the bladder. Typically, but not exclusively, the upper region of the tubular segment is configured and sized for placement in the renal cavity.

Typically the elongated tail member comprises at least one (and more preferably at least two) thread filament(s). Two or more of the filaments may be configured in at least one filament loop, and, advantageously, the tail comprises no unlooped filaments, so that the tail is free from loose ends. The loop(s) can be made by joining the ends of a single filament, in which case the filament loop comprises a junction of individual filament ends, which junction typically is positioned at the point where tail joins to the elongated tubular segment. Preferably, the tail is long enough to effectively prevent migration of the entire tail into the ureter, and the tail has a smaller outer diameter than the outer diameter of the tubular segment.

The tubular stent segment is stiff enough to avoid crimping during insertion through the ureter, so that it can be inserted by typical procedures. The tail, on the other hand, is extremely flexible (soft) in comparison to the tubular segment, and it has a much smaller diameter than the tubular segment to avoid discomfort. Even quite thin structures will provide urine transport, and the thinner and more flexible the tail is, the less likely it is to cause patient discomfort. On the other hand, the tail (and its connection to the rest of the stent) should have sufficient strength so the stent can be retrieved by locating the tail in the bladder and pulling on the tail to retrieve the stent from the kidney and ureter. Details of the tail size are discussed below. The use of reinforcing materials (e.g., sutures as described below) permits the use of thinner tails while still providing the ability to locate the tail in the bladder and to retrieve the stent. The tail may be a suture, and the suture may be coated to avoid encrusting.

The external urine-transport surface of the tail can be convex (circular or oval in section), concave or flat. The tail filament may be fluted. The tail may, but need not, include an accurately shaped anchor segment to control migration up the ureter. The tail may be either solid or hollow; even when hollow, it is not designed to transport a significant amount of urine internally. The tail may also be tapered.

The upper region of the tubular segment may have a portion designed for placement in the renal cavity, which portion has enlarged diameter and/or straight sides and corners. The stent may include an extractor thread attached to the lower end of the elongated tail member.

To make the stent, the tail may be molded in one piece with the tubular segment, or it may be made separately and attached to the bladder end region of the tubular segment at a point toward the kidney from the bladder end of the lower region of the tubular segment. In one specific embodiment, the tail is attached near or at the bladder end of the bladder end region of the tubular segment. The stent may include a suture securing the tail to the tubular segment, and the suture may be incorporated into the tail to impart strength to the tail so the tail may be used to retrieve the stent. If the tail includes a hollow lumen, the suture may be positioned inside that lumen. The suture may be attached to the tubular segment at a point in the bladder end region of the tubular segment, and the suture may extend from the point of attachment through an opening in the bladder end region to the central lumen of the tubular segment and from there to the hollow tail. Alternatively, at least the bladder end region of the tubular segment may include two lumens, a main urine-transporting lumen and a bladder lumen to encase the suture, so that the suture does not become encrusted.

The outer diameter of the tubular segment can be tapered so that it decreases approaching its lower region. The lower region of the tubular segment may include multiple openings positioned, e.g., axially along include its length or radially around its circumference, or in other patterns. In addition, the outer diameter of the stent's tubular segment may decrease approaching the upper region. In other words, the maximum diameter may be at the site of the injury to encourage a sufficiently large inner diameter in the repaired structure, and the tubular segment's outer diameter may decrease moving away from that point of maximum diameter to sections of the normal ureter that are not in need of a broad support structure. Typically, the outer diameter of the upper end of the tubular segment will be greater than the outer diameter of the bladder end. The upper region may include multiple openings (inlets).

In an alternative embodiment, the elongated external urine-transport surface is a continuous surface extending from the kidney to the bladder, e.g., it is the outer surface of a solid member extending from the kidney to the bladder.

Another aspect of the invention features a method of introducing a ureteral stent (described above) into a patient, by (a) positioning the kidney end region of the tubular segment within the renal pelvis; and (b) positioning the elongated flexible member(s) in the bladder.

Yet another aspect of the invention features a method of manufacturing a ureteral stent as described above. The method comprises: (a) providing a polymer pre-form having a tubular shape; (b) forming an elongated tubular stent segment from the polymer pre-form, and (c) providing tail member(s) at an end region of the tubular segment designed to be positioned toward the patient's bladder.

As described in greater detail below, the stent may be manufactured from a polymer form having a tubular shape by forcing the form onto a mandrel to produce the desired three dimensional shape (coils, etc.). The elongated tubular member(s) is attached to one end of the tubular member(s) using sutures as described above. Heat treatments to fuse the structures and/or standard adhesives may be used. Alternatively, the tubular member(s) and the elongated member constitute a one-piece stent.

The use of relatively thin, flexible elongated member(s) to assist urine flow across the ureterovesical junction and into the bladder may reduce reflux and irritation and thereby reduce patient discomfort and medical problems associated with ureteral stents.

Other features and advantages of the invention will appear from the following description of the preferred embodiment, and from the claims.

BRIEF DESCRIPTION OF THE DRAWINGS

FIG. 4A is a view of an alternate embodiment of the stent in FIG. 1, and FIG. 4B is a section taken along 4B—4B of FIG. 4A.

DESCRIPTION OF THE PREFERRED EMBODIMENTS

Figure 1:
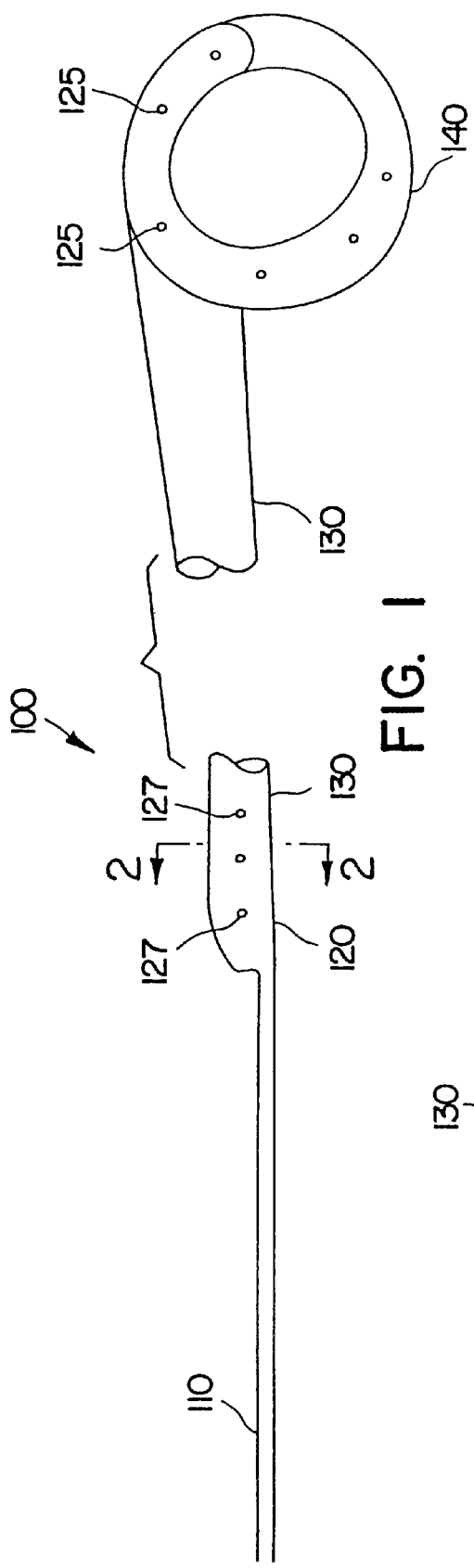
FIG. 1 is a side view of a ureteral stent with a central portion of the tubular segment omitted.

In FIG. 1, ureteral stent 100 includes an elongated tubular body 130 connecting coil end 140 to straight end region 120. Tubular body 130 is designed to extend from the renal pelvis through the ureter to a terminus upstream of the bladder. Tail 110 is attached to straight end region 120, and tail 110 extends along the ureter, across the ureter/bladder junction and into the bladder.

The two opposing end regions 120 and 140 of elongated tubular body 130 are illustrated in FIG. 1. Coiled end region 140 is designed to be placed in the renal pelvis of the kidney. For illustrative purposes, coiled end region 140 is shown with a pigtail helical coil although any shape that will retain the stent in place within the kidney will do. Coiled end region 140 includes several openings 125 placed along the wall of the tubular body; the openings may be arranged in various geometries (e.g., axial, circumferential, spiral). The entire tubular segment, including the region between the kidney and the bladder end regions, may include additional openings.

The bladder end region 120 of the tubular stent segment is designed to terminate in the ureter, upstream of the bladder. For purposes of further description, the end region of stent 100 received in the kidney will be designated the kidney end and the opposite end of stent 100 toward the bladder will be termed the bladder end.

Figure 2:
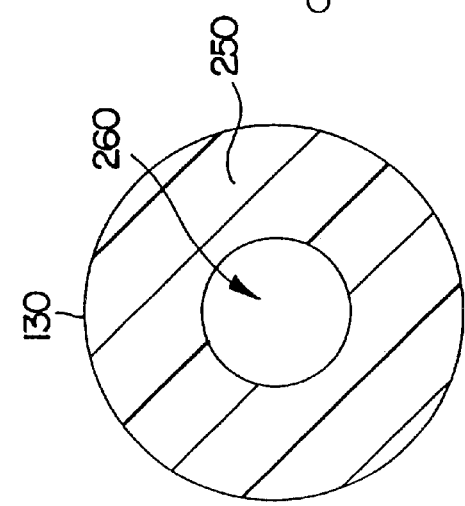
FIG. 2 is a cross-sectional view along line 2—2 in FIG. 1.

FIG. 2 is a cross-sectional view of stent 100 of FIG. 1. In FIG. 2, elongated tubular body 130 has annular walls 250 having an inner and outer diameter. The outer diameter of tubular body 130 may be substantially uniform throughout much of the length of the tube, or it may taper from a relatively short region of larger diameter (the site of the repair, where there is a risk that the healing process will substantially restrict flow in the lumen) to a region of generally small diameter. The precise configuration may depend on the ureteral defect being corrected. Just one of the many classes of procedures that can benefit from the stent are endopyelotomies—procedures for treating ureteropelvic junction (UPJ) obstruction by an incision which perforates the ureter at the stricture. In these and other procedures, the stent keeps the ureter lumen open during the healing process, so that the inner diameter of the resulting healed structure is adequate. The section of the tubular segment at the defect is large enough to support growth of repair tissue having an adequate inner diameter. At other sections of the ureter (e.g., sections not being surgically repaired), the outer diameter of the tubular segment may be far smaller, but with an inner diameter adequate for passage over a guidewire. For example, the outer diameter of the bladder end region of the tubular segment typically is 2Fr.–12Fr. Preferably the outer diameter of tubular body 130 is greatest at the ureteropelvic junction obstruction but begins to taper approaching each end. Alternatively, for a patient with an upper ureteral obstruction, the upper (kidney) portion of the tubular member 130 may be uniform in diameter, tapering just in the lower (bladder) portion.

Tubular member 130 defines a central lumen or passageway 260, extending from kidney end region 140 to bladder end region 120. The inner diameter of lumen 260 is sufficient to permit passage over a guidewire. Tubular body 130 may also have openings 125 extending through its walls 250 to facilitate the flow of urine from the kidney into central lumen 260 and openings 127 to facilitate flow out of central lumen 260.

Figure 3:
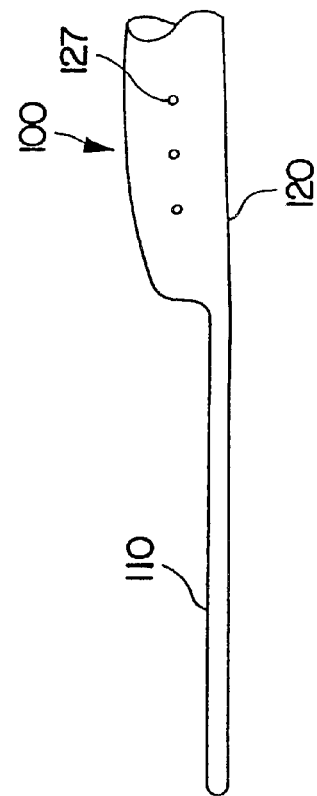
FIG. 3 is an enlarged side-view of a portion of the ureteral stent in FIG. 1.

In FIG. 3, the outer diameter of elongated tubular body 130 tapers near bladder end region 120. The outer diameter of bladder end region 120 may be made as small as possible while maintaining the ability to pass over a guidewire. Elongated tubular body 130 may (but need not be) substantially straight in bladder end region 120, i.e. it does not coil or curve in the absence of external force. When tail 110 is a single filament, it typically is thinner than even the smallest portion of bladder end region 120 of the tubular stent segment. Alternatively, it may be desirable to design the tail from multiple filaments, each of which, by itself, is much thinner than the bladder end region of the tubular stent segment. Together, such a multi-filament tail has a larger effective diameter, providing additional bulk while maintaining comfort. Tail 110 may be attached at or near the end of region 120, and it extends from that attachment into the bladder. Tail 110 is either solid or hollow. It can be generally cylindrical in shape; alternatively, it can be fluted, concave (quarter-moon)-shaped or it may assume other shapes.

The tail can have an outer diameter that is significantly less than the inner diameter of the ureter (typically 2–5 mm) and no greater than the outer diameter of the tubular segment from which it extends. For example the tail diameter is less than 10Fr. and as low as a suture (about 0.5Fr). Preferably the tail diameter is between 2Fr. and 4Fr. The length of tail 110 is preferably between 1 and 100 cm. In one embodiment, the tail is long enough so that at least a portion of it will remain in the bladder, and effectively the entire tail cannot migrate up into the ureter. Preferably the length is between 1 and 40 cm. Tail 110 is flexible and, upon application of force, can be curved, but also has memory such that when the force is removed, it is generally straight.

Stent 100, including tail 110 and tube 130, may be a single unit. Thus, tail 110 can be a unified piece, extending from bladder end region 120 with no additional attachment means. Alternatively tail 110 can be secured to elongated tube 130 or bladder end region 120 by physical or mechanical methods.

For example, in FIG. 4A, a suture 415 is inserted through an opening 418 in the tubular member and then threaded through the lumen 417 of tubular member 430. In FIG. 4B, tail 410 is a hollow member having suture 415 threaded through its inner lumen 412.

Figures 5A, 5B:
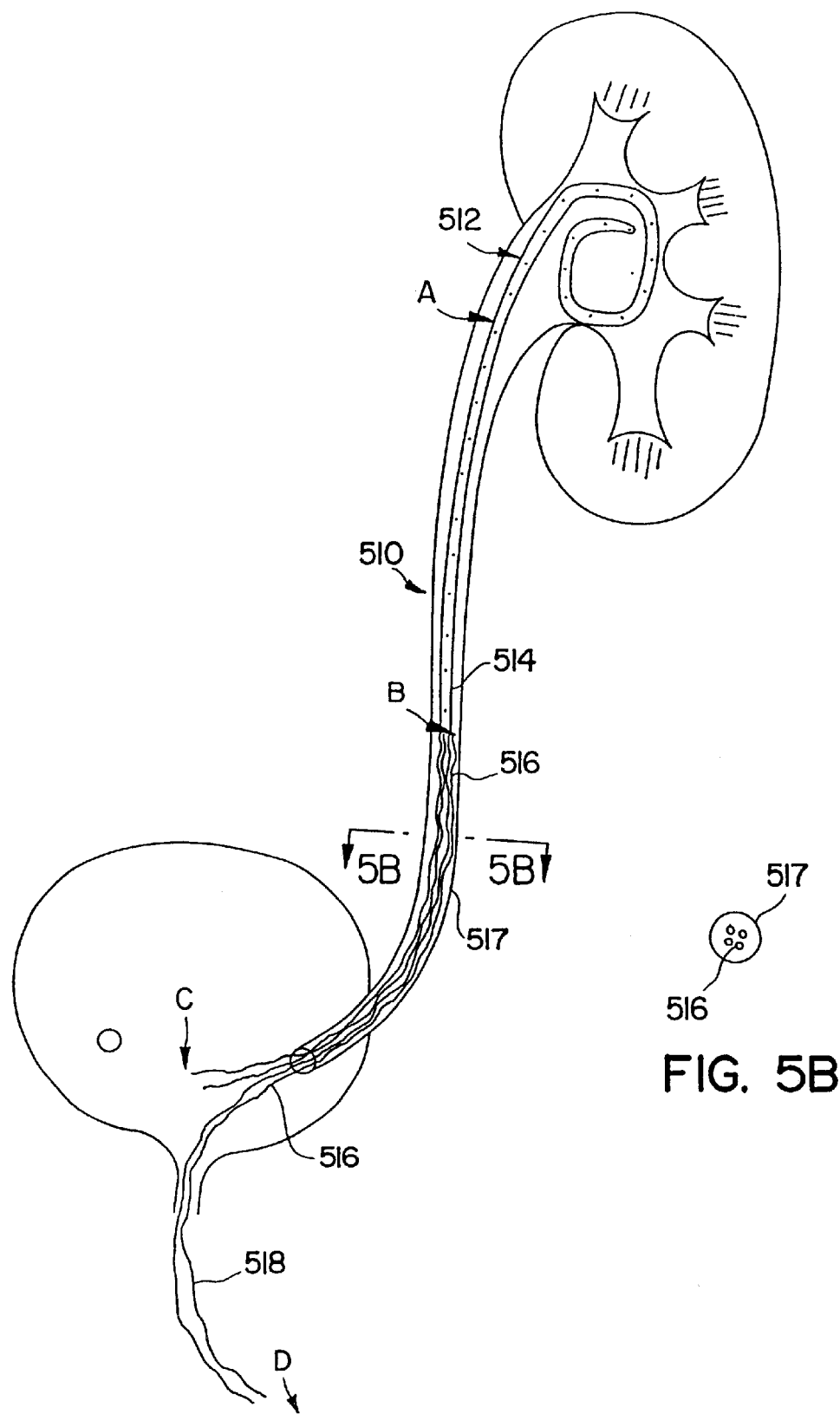
FIGS. 5A and 5B are schematic representations of another stent according to the invention, depicted in place.

FIG. 5 is a schematic of another stent 510. The kidney end A of the stent has a pre-formed memory bend, to coil 512 as shown. Kidney end A is larger and more rectangular to help prevent upward as well as downward stent migration. End A may be closed or tapered to accommodate various insertion techniques. For the upper portion (A—B) of the stent, diameter, lumen size, perforations and materials are conventional. The lower end 514 of the tubular stent segment ends at B. The distance A—B could vary depending on the patient's anatomy. At B, the stent is tapered (or at least smooth and constant in diameter).

Two or more monofilament or coated (plastic or silicone) threads 516 exit from the lumen or from the stent wall. These threads only partially fill the ureter and are as flexible (soft) as possible. Typically, they are cut to a length which forces confinement within the bladder.

The portion of the upper segment 512 lying within the renal pelvis (e.g, from the kidney end of the stent to point A) is expanded so that it is larger in section, and it may even be oval or rectangular in cross-section, to help prevent upward as well as downward stent migration. The kidney end of the stent may be closed and/or tapered to accommodate the desired insertion technique. The upper portion 512 is made of a relatively stiff material (among the materials currently used in ureteral stents), and it should be designed to effectively restrict the motion of the stent to prevent proximal as well as distal migration of the catheter during normal physiological activity (required because the lower preformed portion is deleted). The length of the straight portion of the upper segment (FIG. 5A point A to B) will vary with patient size and anatomy. In the preferred configuration, the upper segment extends more than halfway down the ureter when in proper position. The lowest end of the upper segment (FIG. 5A point B) should be tapered or beveled to facilitate withdrawal. Otherwise, the upper segment is a typical stent in diameter, materials and shape.

The lower segment (FIG. 5A point B to point C) consists of two or more (e.g four) monofilament, plastic coated or silicone coated threads (shown in section in FIG. 5B) which extend from the lumen or sidewall of the lower end of the upper segment (FIG. 5A point B) along ureter 513 into the bladder. These threads are extremely flexible, and their diameter is selected to maintain a passage for urine flow and yet drastically reduce bladder and ureteral irritation. By avoiding distortion of the ureter wall, the threads may inhibit urinary reflux as well. The threads should be long enough to reach well into the bladder (FIG. 5A point C), but not so long as to wash into the urethra with voiding. One thread 518 (or two or more threads in a loop) may be long enough to exit through the urethra (FIG. 5A point B to point D) to permit ready removal by pulling (avoiding cystoendoscopy).

These extended threads may also be used for stent exchange, in which a second catheter is exchanged for the catheter already in place. According to that procedure, these extended threads are captured with a snare that has been inserted through the central lumen of a second catheter. The snare is used to pull the threads through the lumen as the second catheter is advanced into the ureter. A guidewire is then inserted through the central lumen of the second catheter to the kidney (outside the first catheter's tubular body). The first stent is then removed by pulling on the threads, leaving the guidewire in position for placement of a new stent using standard techniques.

Figure 6A:
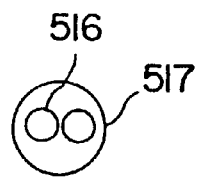
FIGS. 6A–6D depict alternative cross-sections of the tail of a stent according to FIG. 5.
Figure 6B:
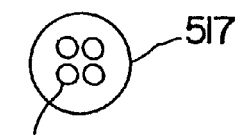
Figure 6C:
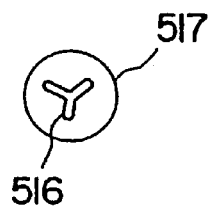
Figure 6D:
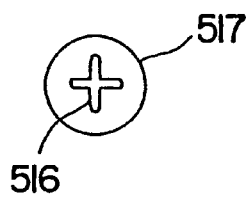

FIGS. 6A–6D are alternative cross sectional sketches (taken at the same location as FIG. 5B) of some possible arrays of threads passing within the lower ureter 517. Multiple threads 516 (2 and 4, respectively) are shown in FIGS. 6A and 6B. A substantially similar conduit could be achieved by fluted type cross sections in a single filament FIGS. 6C and 6D). The shapes of FIGS. 6C and 6D could also be effective in reducing stiffness and hence irritability at the bladder end (i.e., lower segment), e.g., in a single filament design. Multiple threads may have the advantage of better surgical manipulability and superior comfort to the patient.

Figure 7A:
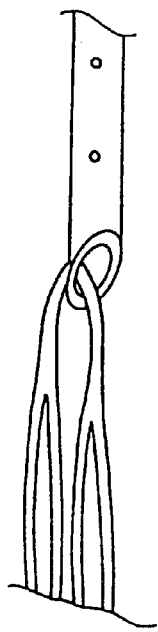
FIG. 7A is an enlargement of a portion of FIG. 7.
Figure 7:
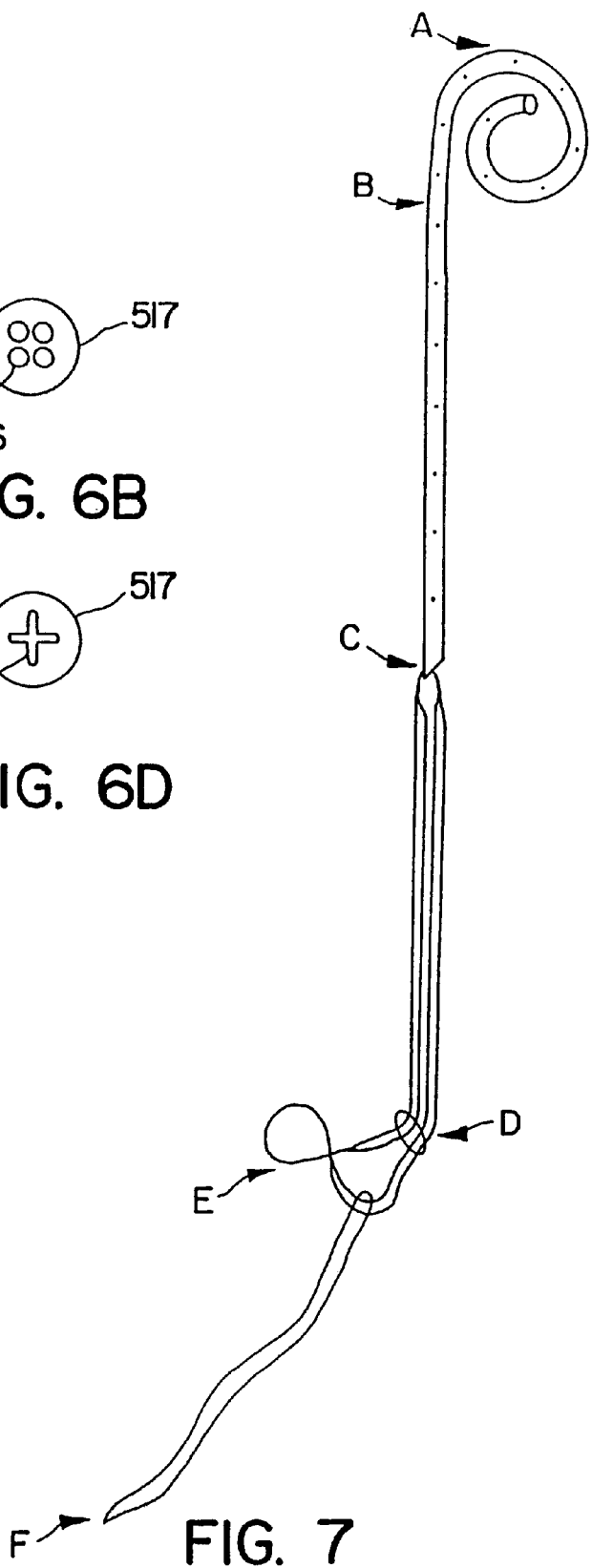
FIG. 7 is a schematic representation of yet another stent according to the invention, having an extraction thread.
Figure 8:
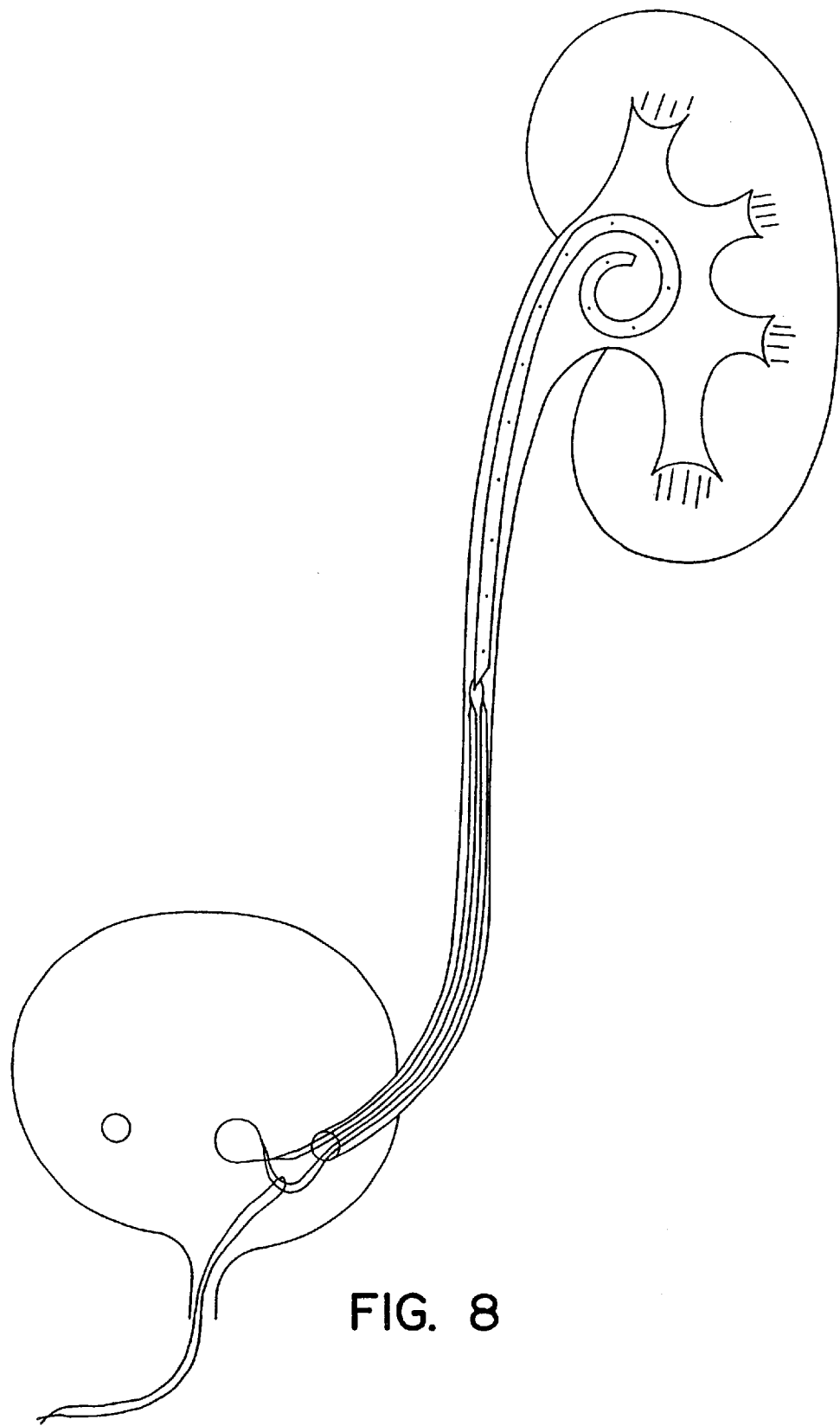
FIG. 8 is a schematic representation of the stent of FIG. 7 shown in position.

Further refinements are described below and in FIGS. 7 and 7A which deal with: a) proximal or upward stent migration of either the entire stent or individual threads in the lower segment independent of upper segment movement; b) bunching of one or more threads within the ureter so as to obstruct flow or cause ureteral injury or knotting at the time of removal; and c) in multi-thread embodiments, discomfort and/or reduced drainage through the ureter resulting from the use of threads of different lengths. In FIGS. 7, 6 F (F=French size=circumference in mm) stent is a generally a good size for adult urinary systems. It is large enough to provide good drainage and small enough to minimize local irritation and inflammation of the ureter. In this embodiment, the upper segment need be only a single loop of conventional size because a change in the design of the lower segment (see later discussion and FIG. 8) should prevent proximal migration. The upper segment (FIG. 7 point A to point C) is constructed of a relatively firm material because, during insertion, the pusher tubing should be removed after the guidewire is removed. This means that there will be some drag on the threads during removal of the pusher tubing which could dislodge the stent if the coil (FIG. 7 point A to point B, about 2.5 cm) does not provide adequate resistance. The coil may be tapered or closed depending on the insertion technique desired (i.e., over a previously placed guidewire.

FIG. 7 point B to point C should have an approximate length of 12 cm. This is long enough to prevent dislocation of the upper segment in a large renal pelvis and short enough to end well above the point where the ureter crosses the common iliac vessels. At the iliac vessels, the ureter takes a fairly sharp turn and the threads will more easily follow the natural curves at this point. This design should reduce the inflammation that is normally seen in this region when a conventional double-J stent is left indwelling on a chronic basis.

Figures 8A, 8B:
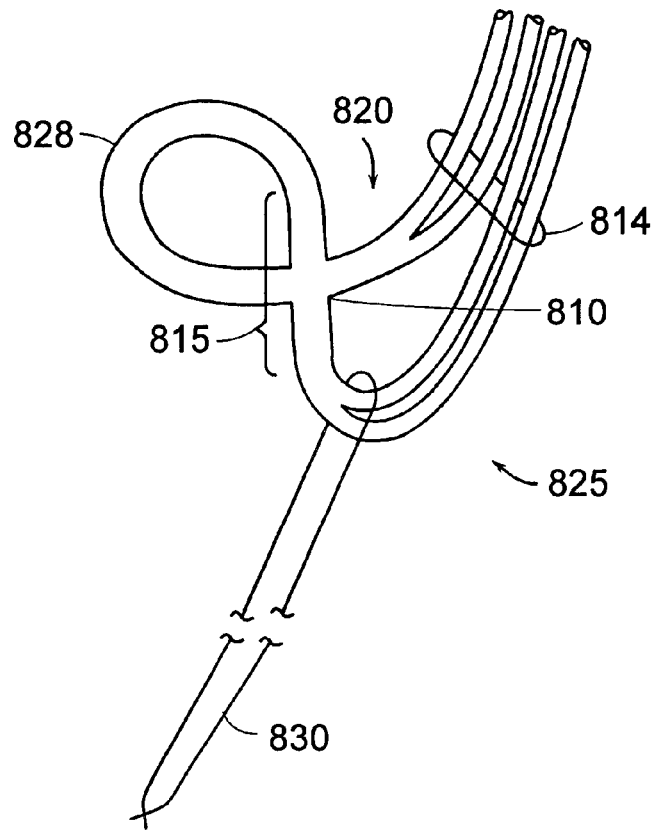
FIG. 8A is a detail of the connection between the tail and the extraction thread.
FIG. 8B is a cross-section of threads of differing softness, showing the effect of compression on interstitial space.

The junction of the upper and lower segments at FIG. 7 point C is important. See FIG. 7A, which enlarges this junction. At point C (FIG. 7) the threads are attached to the upper segment in a manner that achieves the following goals: 1) the threads are securely attached to the upper segment and to each other (at least for a short distance of about 0.8 mm) so that their orientation to themselves is maintained (to the maintenance of lower end asymmetry); 2) the threads do not obstruct the lumen of the upper segment and they allow for the easy passage of a standard guidewire (e.g., 0.035 guidewire); 3) the transition diameters in this region closely preserve the 6F standard so that this point can pass in both directions smoothly throughout the instruments used for insertion and through the ureter; 4) there is no cause for a localized ureteral obstruction; and 5) there is an effective abutment for the pusher tubing. For an average size ureter a good starting string diameter for a four string lower segment (FIG. 7 point C to point E) would be 0.020 inches. A simple monofilament nylon thread is an easy potential solution but may be too stiff. A more supple monofilament or woven thread with silicone or other coating may be required to achieve minimal irritability. However, the threads should be sufficiently resistant to compression so that tissue generated pressures cannot collapse the interspaces of the threads. See FIG. 8B, showing cross-sections of threads (left) which retain interstitial space under some modest compression and of threads (right) which are so soft that they compress into a plug with reduced interstitial space. These threads may have centimeter markings beginning at a point no more than 20 centimeters from point B (FIG. 7) so that functional ureteral and total stent length may be noted.

The portion of the lower segment which lies within the bladder when the stent is in proper anatomic position (FIG. 7 point D to point E) is important to, both comfort and function. Proximal migration can be controlled by using asymmetrical lengths of the thread pairs, with one pair being 2 cm longer than the other pair, so that the fused junction 810 of these threads tends to intersect with the ureteral orifice 814 at an angle (e.g., ~90°) with the stiffened area 815 having a length of 6 mm (see detail FIG. 8A). In the ideally fitted stent of this embodiment, the thread pairs will extend beyond the ureteral orifice (FIG. 7 point D) by 1 cm at the short limb 820 and 3 cm at the long limb 825. However, this lower segment configuration allows for considerable tolerance in sizing (unlike unsecured independent threads which must be selected to have a length so as to avoid upward migration of the thread through the ureteral orifice 814) and a chosen length which is 1 cm shorter or 2–3 cm longer than the ideal length should be satisfactory. Using this configuration the threads should form a continuous loop 828 of 3.5 cm length to prevent free ends from poking the bladder wall or prolapsing through the urethra. Buoyant threads may add to patient comfort, because they will float away from the trigone region of the bladder, where most of the sensory nerve fibers are located. A typical small gauge filament extraction thread 830 may be attached to the longer limb 825 of the thread pairs, which is a suitable pulling point for removal.

From this embodiment, a small diameter pusher tubing of 4–4.5F should be used to aid insertion. Soft percuflex is near optimal for the lower segment, and firm or regular percuflex is used for the upper segment.

The bladder end should be easily inserted using instruments, and it should prevent proximal migration of the stent. The design of FIG. 7 will avoid tangling and migration of the stent. Alternatively, soft percuflex, for example, has good resistance to extreme flexion at small radii (e.g., even 0.020" diameter) so that a simple continuous loop extending from the junction of the upper and lower segments (see FIG. 9) may be adequate to prevent upward migration. The design of FIG. 9 also has the advantage of relative ease of manufacture and relative ease of insertion, as well as ease and comfort of removal.

Other dimensions that can be used (without limitation) are 12 cm straight portion of the upper hollow shaft, and 12 cm, 14 cm, or 16 cm length of added loops of soft percuflex. For the 0.020" diameter material, either 2 or 3 loops may be used providing 4 or 6 strings, total. For 0.040" inch material, either 1 or 2 loops is recommended.

Figure 9:
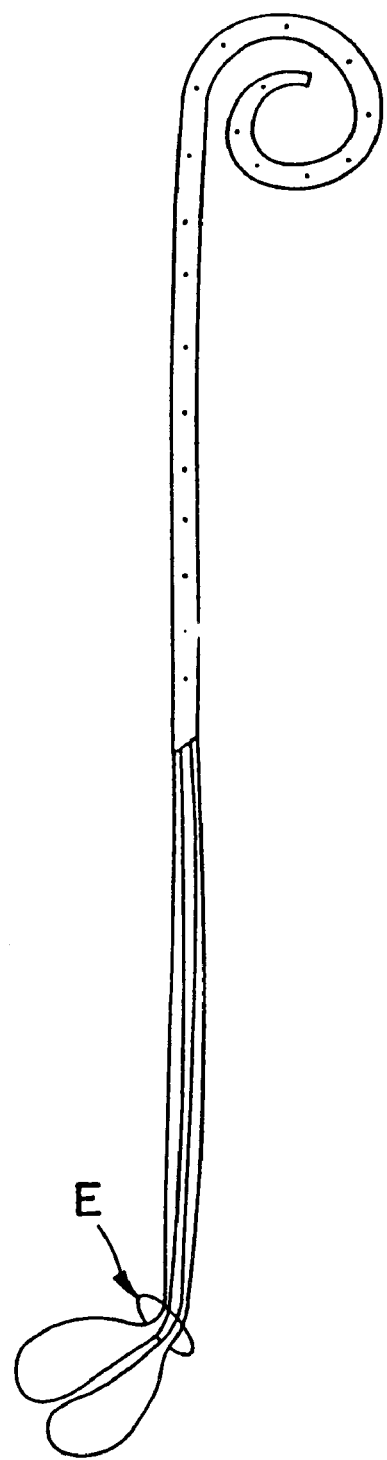
FIG. 9 shows an alternative embodiment of the stent.
Figure 10:
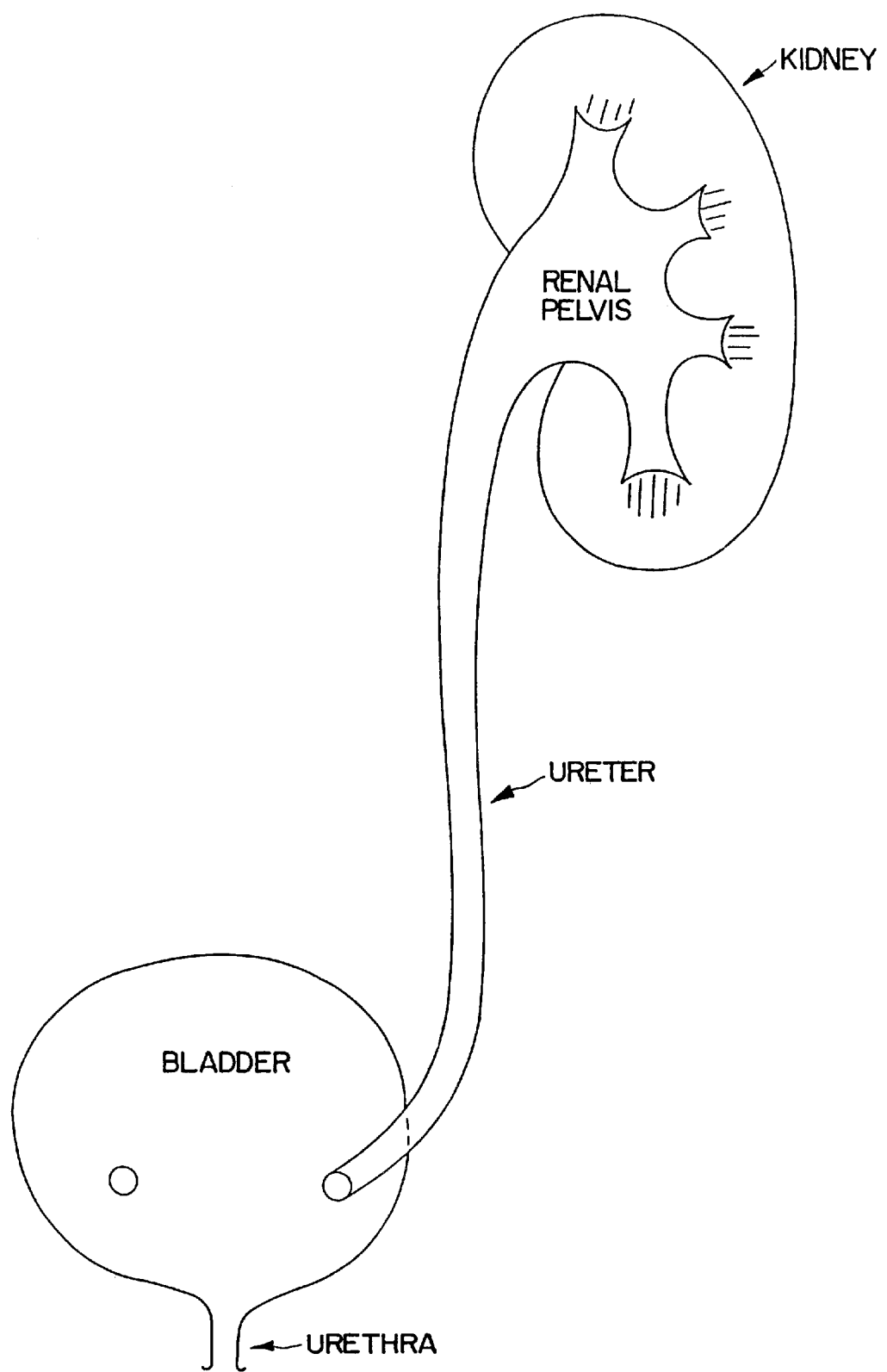
FIG. 10 is a schematic drawing of the human urinary tract without a stent, showing the renal pelvis, the kidney, the ureter, and the ureteral orifices opening into the bladder.
Figure 11:
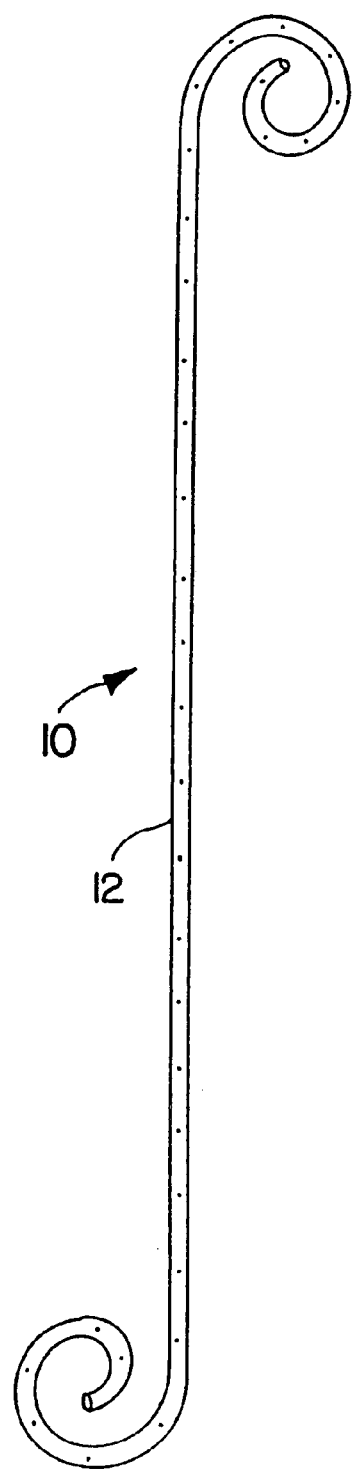
FIG. 11 depicts a prior art double-J stent outside the body.
Figure 12:
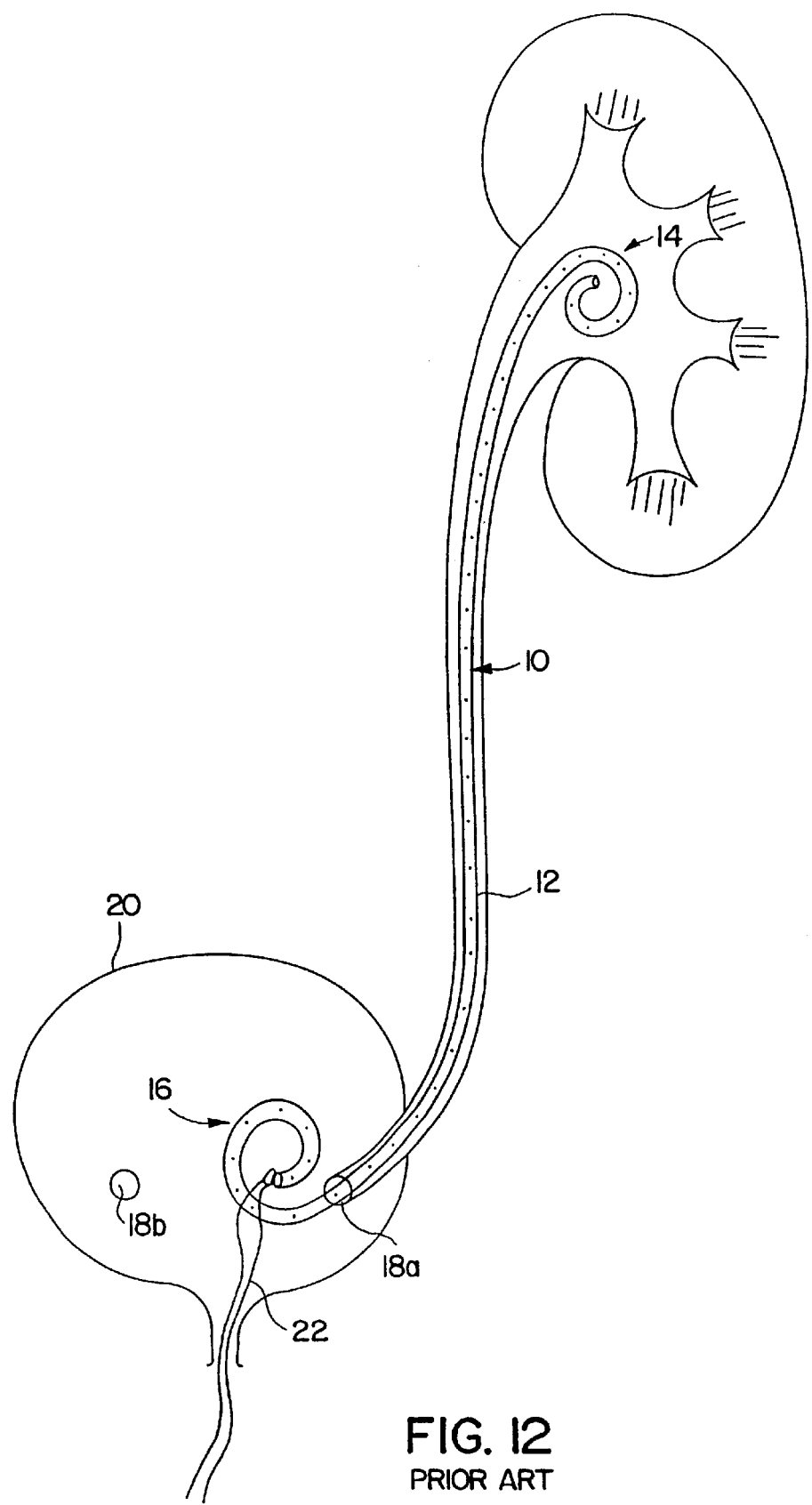
FIG. 12 depicts a prior art J indwelling ureteral stent in position.

FIG. 9 shows such an alternative embodiment having a simple coil at the kidney end. The lower end is constructed of looped stringlike elements with ends fused at the junction between the lower and the upper end. Therefore, there are an even number of string elements, with no free ends. Circle E in FIG. 9 represents an idealized depiction of the ureteral opening into the bladder. While not shown in FIG. 9, the loops may be fused over a very short distance at the bladder end in order to prevent tangling of loops and to improve stent handling. Any conventional means of fusion may be used. Optionally, organization of the loops can be maintained by pre-placing them inside the pusher tubing using a long monofilament nylon loop tail, similar to those used for the non-invasive removal stents (i.e. without sensor endoscopy).

Methods for insertion and removal of ureteral stents are known in the art. Generally, stent placement is achieved by advancing the tubular stent segment over a guidewire in the ureter. A pushing catheter passes the tubular segment into the kidney, while maintaining the tail in the bladder. Other methods such as a stiff sheath can be used to position the stent. Once in position, the sheath can be removed.

The tubular portion of the stent may be manufactured by extruding a tube according to known techniques. The elongated tail may be separately manufactured by conventional techniques and attached to the tubular portion, e.g., using biocompatible adhesive materials or heat. Alternatively, the stent may be made by injection molding the tube and the tail as a single piece, using a pin to create hollow segments. The stent may be manufactured from any of a number of biocompatible polymers commonly used inside the body, including polyurethane and polyethylene. In still other embodiments, the entire stent may be solid, so that urine is conveyed entirely on an external stent surface.

What is claimed is:

1. A ureteral stent for assisting flow of urine, the stent comprising:
   i. an elongated tubular segment extending from an upper region including at least a first opening to a lower region having an external surface and including at least a second opening, the lower region having a length sufficient to be positioned in a ureter when the ureteral stent is in use, and defining a lumen extending therethrough connecting the first opening to the second opening;
   ii. a coiled end region extending distally from the upper region of the tubular segment to be positioned substantially in a kidney when the ureteral stent is in use; and
   iii. a thin flexible elongated tail having an external urine-transport surface, the thin flexible tail being substantially straight and tapering to a smaller outer diameter as it transitions from the lower region of the tubular segment so as to receive urine from the lower region of the tubular segment and to transport the urine along the urine-transport surface, and including a transition from the external surface of the lower region of the tubular segment to the urine-transport surface of the thin flexible tail that is continuous.

2. The stent of claim 1 in which the external urine-transport surface when the ureteral stent is in use extends along at least part of the ureter, across the ureter/bladder junction, and from there through the ureteral opening into the bladder.

3. The stent of claim 1 in which the thin flexible tail is solid.

4. The stent of claim 1 in which at least part of the tail is hollow.

5. The stent of claim 1 in which the tubular segment includes multiple openings along its length.

6. The stent of claim 1 wherein the external urine-transport surface of the tail is continuous and uninterrupted.

7. A ureteral stent for assisting flow of urine, the stent comprising:
   i. an elongated tubular segment extending from an upper region including at least a first opening to a lower region having an external surface and including at least a second opening, the lower region configured to extend more than halfway down a ureter when the ureteral stent is positioned in the ureter, and defining a lumen extending therethrough connecting the first opening to the second opening;
   ii. a coiled end region extending distally from the upper region of the tubular segment to be positioned substantially in a kidney when the ureteral stent is in use; and
   iii. a thin flexible elongated tail having an external urine-transport surface, the thin flexible tail being substantially straight and tapering to a smaller outer diameter as it transitions from the lower region of the tubular segment so as to receive urine from the lower region of the tubular segment and to transport the urine along the urine-transport surface, and including a transition from the external surface of the lower region of the tubular segment to the urine-transport surface of the thin flexible tail that is continuous.

8. The stent of claim 7 in which the external urine-transport surface when the ureteral stent is in use extends along at least part of the ureter, across the ureter/bladder junction, and from there through the ureteral opening into the bladder.

9. The stent of claim 7 in which the thin flexible tail is solid.

10. The stent of claim 7 in which at least part of the tail is hollow.

11. The stent of claim 7 wherein the external urine-transport surface of the tail is continuous and uninterrupted.

* * * * *